Figure 1:
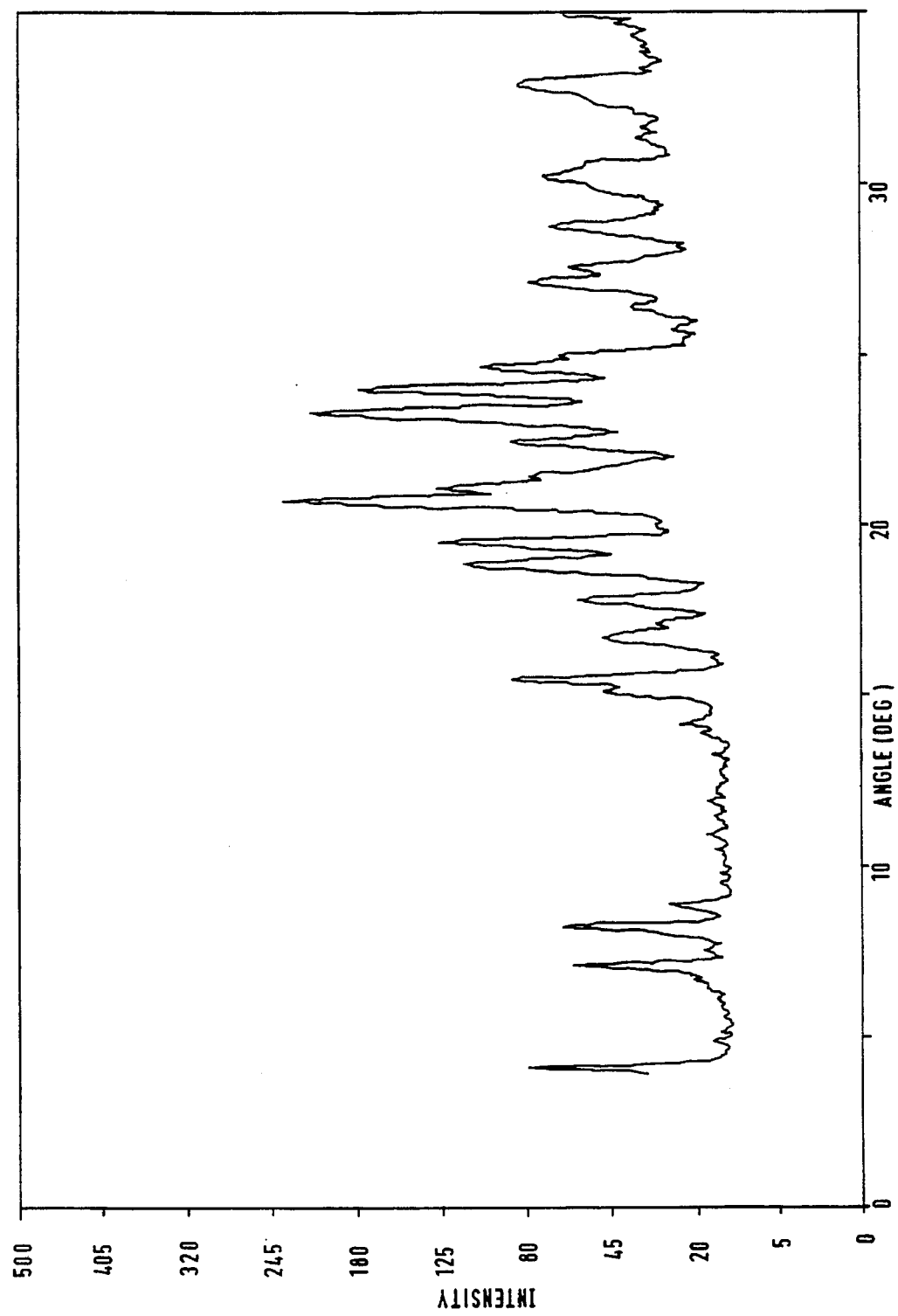

United States Patent [19]

Greenway et al.

[11] Patent Number: 5,594,026
[45] Date of Patent: Jan. 14, 1997

[54] POLYMORPHS OF CRYSTALLINE MUPIROCIN

[75] Inventors: Michael J. Greenway; Sarah D. Salt, both of Worthing; Christopher E. Valder, Hove; Alan D. Curzons, Arundel, all of England

[73] Assignee: SmithKline Beecham Group p.l.c., England

[21] Appl. No.: 424,684

[22] Filed: Apr. 18, 1995

Related U.S. Application Data

[63] Continuation-in-part of Ser. No. 75,454, filed as PCT/GB91/02174, Dec. 6, 1991, abandoned.

[30] Foreign Application Priority Data

Dec. 11, 1990 [GB] Great Britain .......................... 9026873

[51] Int. Cl.$^6$ .......................... C07D 407/06; A61K 31/35
[52] U.S. Cl. ........................................... 514/460; 549/414
[58] Field of Search .................... 549/414; 514/460

[56] References Cited

U.S. PATENT DOCUMENTS 4,222,942  9/1980  O'Hanlon et al. .

FOREIGN PATENT DOCUMENTS

| 0005614 | 11/1979 | European Pat. Off. . |
| 0095897 | 12/1983 | European Pat. Off. . |
| 0251434 | 1/1988 | European Pat. Off. . |
| 1395907 | 5/1975 | United Kingdom . |
| 1577730 | 10/1980 | United Kingdom . |
| 2097670 | 11/1982 | United Kingdom . |

*Primary Examiner*—Nicky Chan
*Attorney, Agent, or Firm*—Wayne J. Dustman; Stephen Venetianer; Edward T. Lentz

[57] ABSTRACT

Two further crystalline polymorphic forms of the anti-infective agent mupirocin have been identified. Processes for the preparation thereof and the use thereof are described.

9 Claims, 7 Drawing Sheets

POLYMORPHS OF CRYSTALLINE MUPIROCIN

This is a continuation-in-part of application Ser. No. 08/075,454, filed as PCT/GB91/02174 Dec. 6, 1991, now abandoned.

This invention relates to polymorphs of crystalline mupirocin, processes for their preparation, and to their use in therapy and as growth promoting agents in animals.

Mupirocin (formerly known as pseudomonic acid) is the compound formula (I):

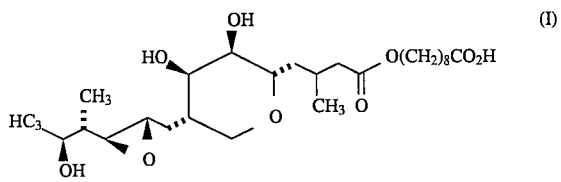

It is an antibiotic produced by aerobically culturing pseudomonas fluorescens (see GB 1 395 907, Beecham Group). The compound exhibits good activity against Gram-positive bacteria, against some Gram-negative bacteria such as H.influenzae and Legionella and against mycoplasma. It is however rapidly metabolised in-vivo to monic acid which is inactive. Mupirocin is marketed as a topical antibacterial agent by SmithKline Beecham under the Trade Name BACTROBAN. This product is an ointment with a polyethylene glycol base in which mupirocin is dissolved (see also EP 0 095 897, Beecham Group). In addition, mupirocin also has been shown to have in certain compositions (in which it is present in an amount which exceeds its saturation solubility in the carrier of that composition) topical anti-fungal activity (see EP 0 251 434, Beecham Group). Furthermore, mupirocin is also known to have a growth-promoting effect in livestock (see GB 2 097 670, Beecham Group).

Prior to the present invention, mupirocin had been obtained in crystalline form as a single polymorph, herein after referred to as Form I, by recrystallization from a solution of mupirocin in ethyl acetate or methyl iso-butyl ketone, or by precipitation from such solutions using heptane, at ambient temperatures. Crystalline mupirocin (FORM I) has a melting point in the range 70°–76.5° C.

It has now been discovered that mupirocin exists in further crystalline polymorphic forms (FORMS II and III) which are distinct from the form (FORM I) previously known, and which forms also have utility in the pharmaceutical and veterinary fields.

Figure 2:
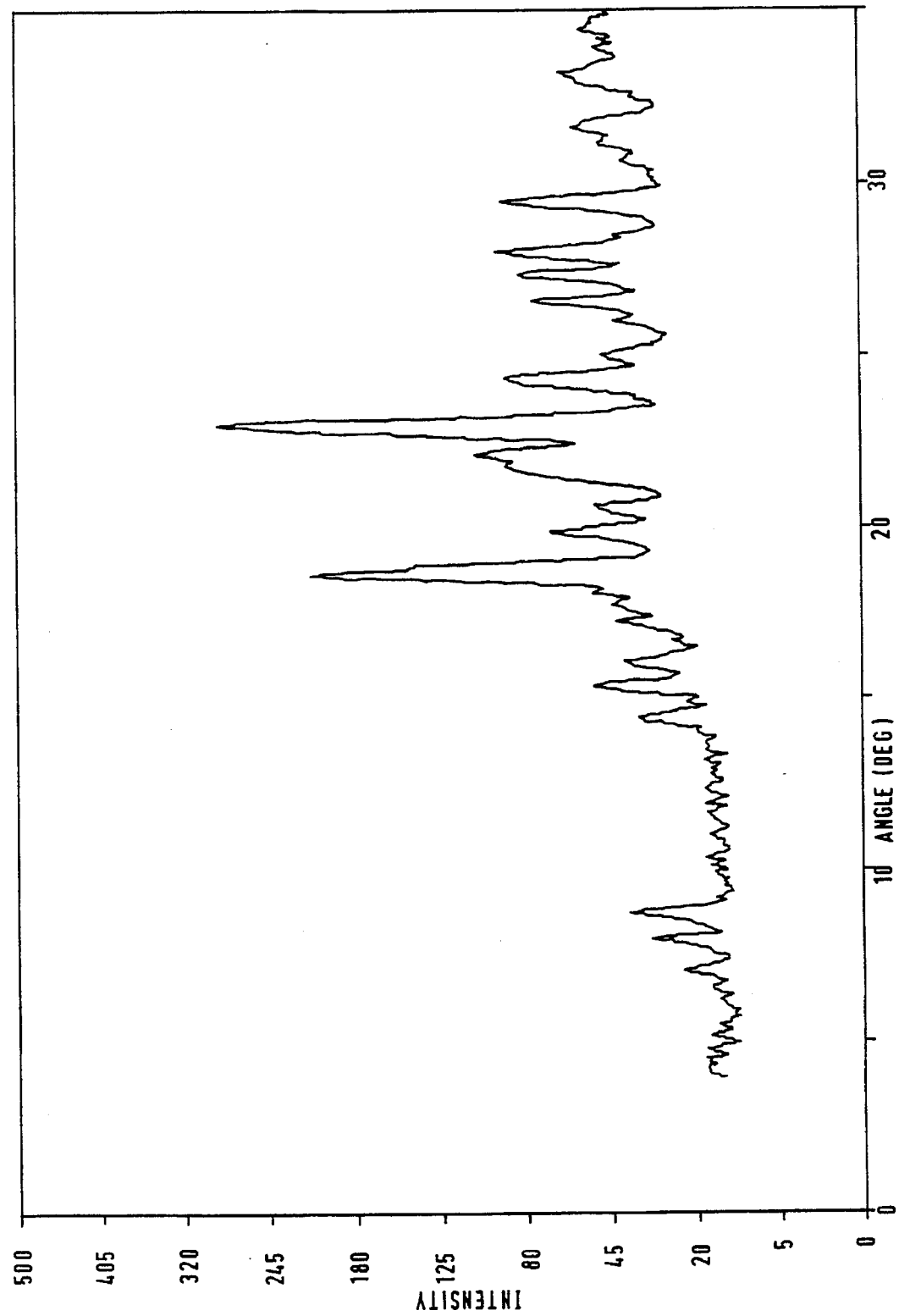
Figure 3:
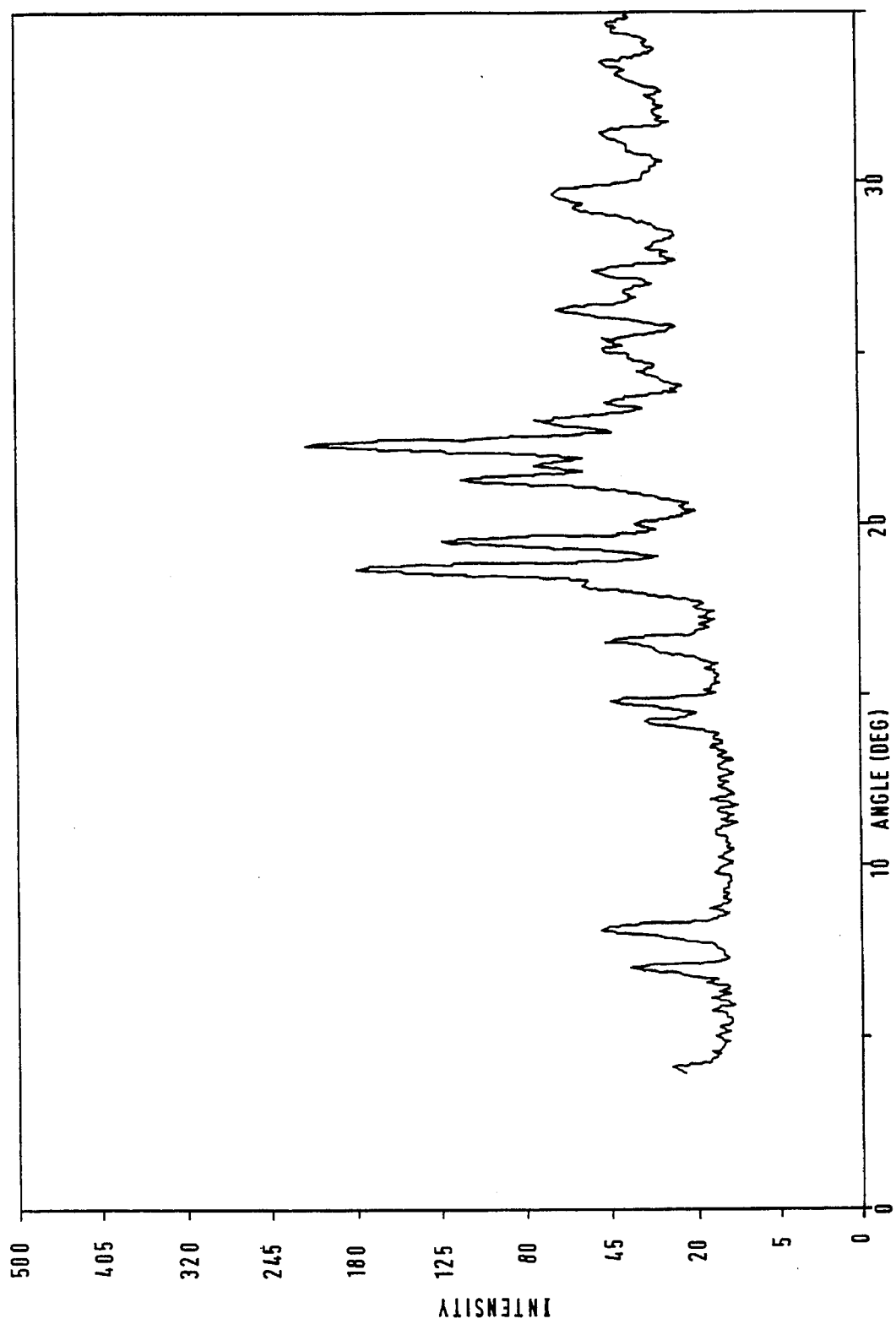
Figure 4:
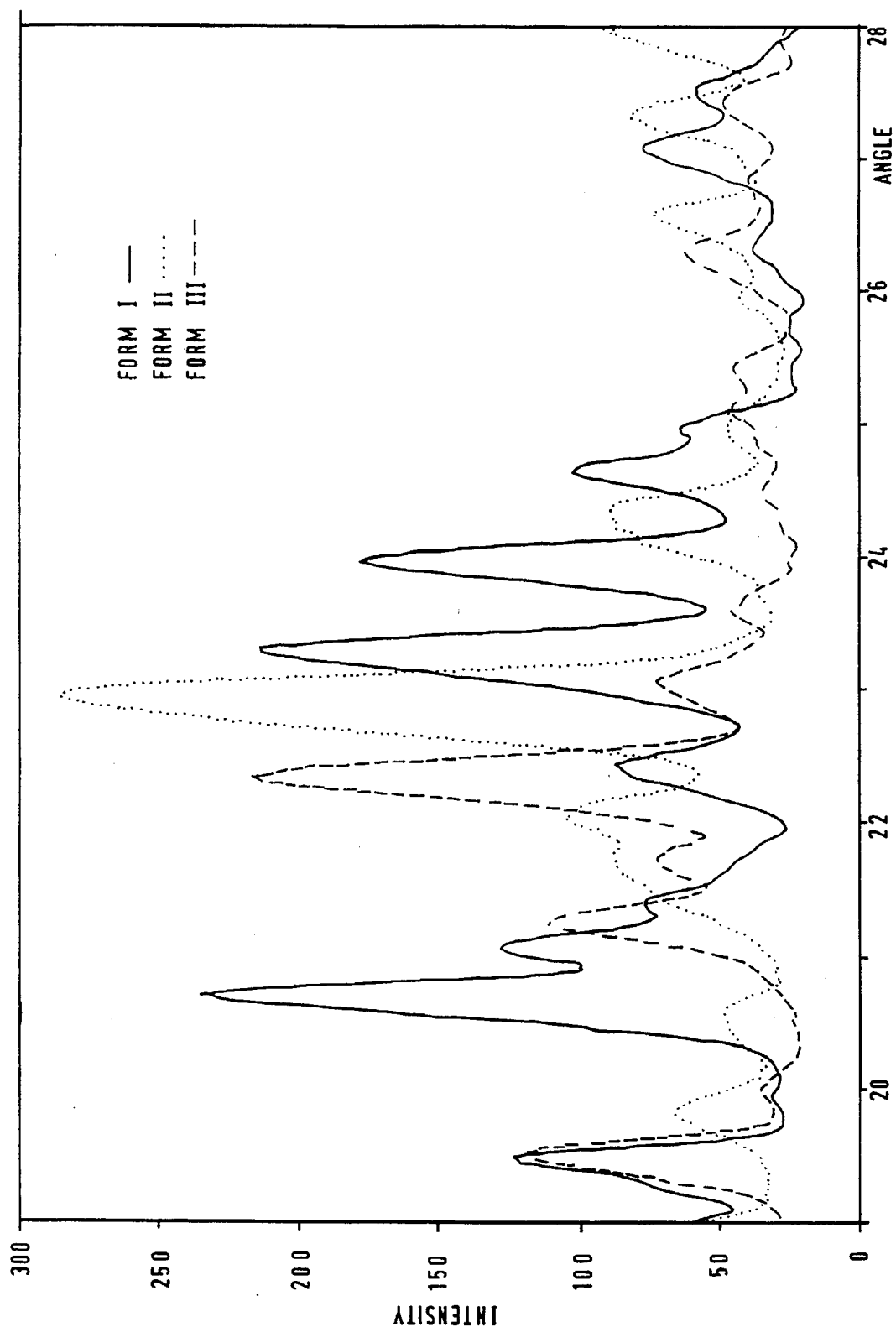
Figure 5:
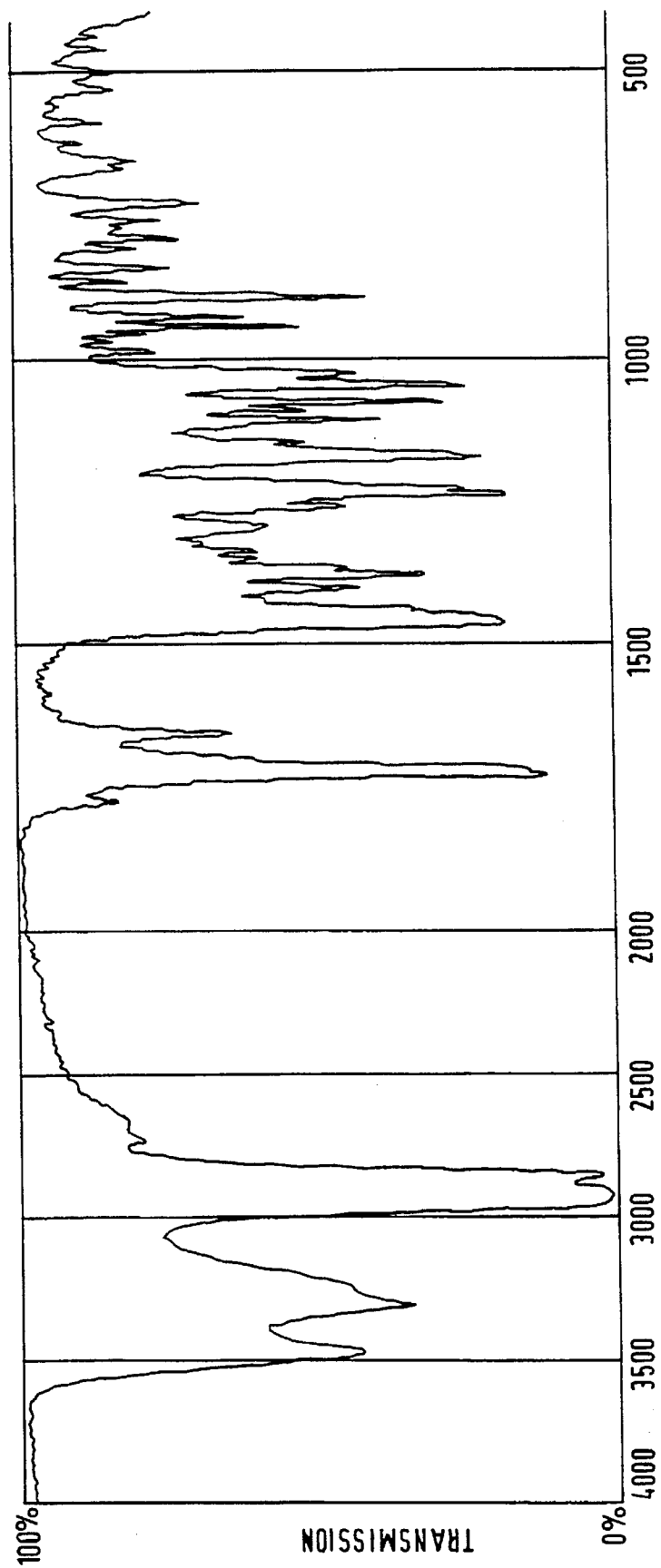
Figure 6:
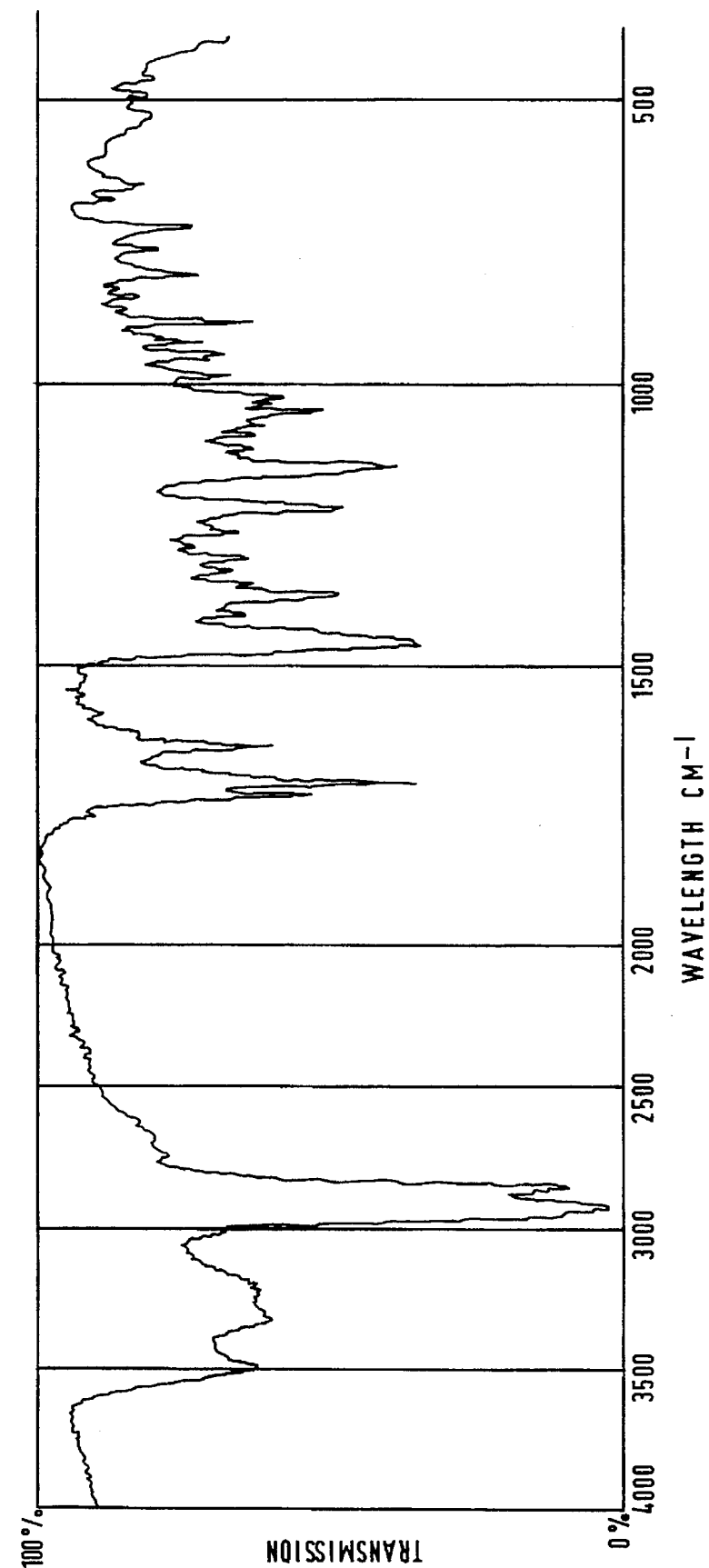
Figure 7:
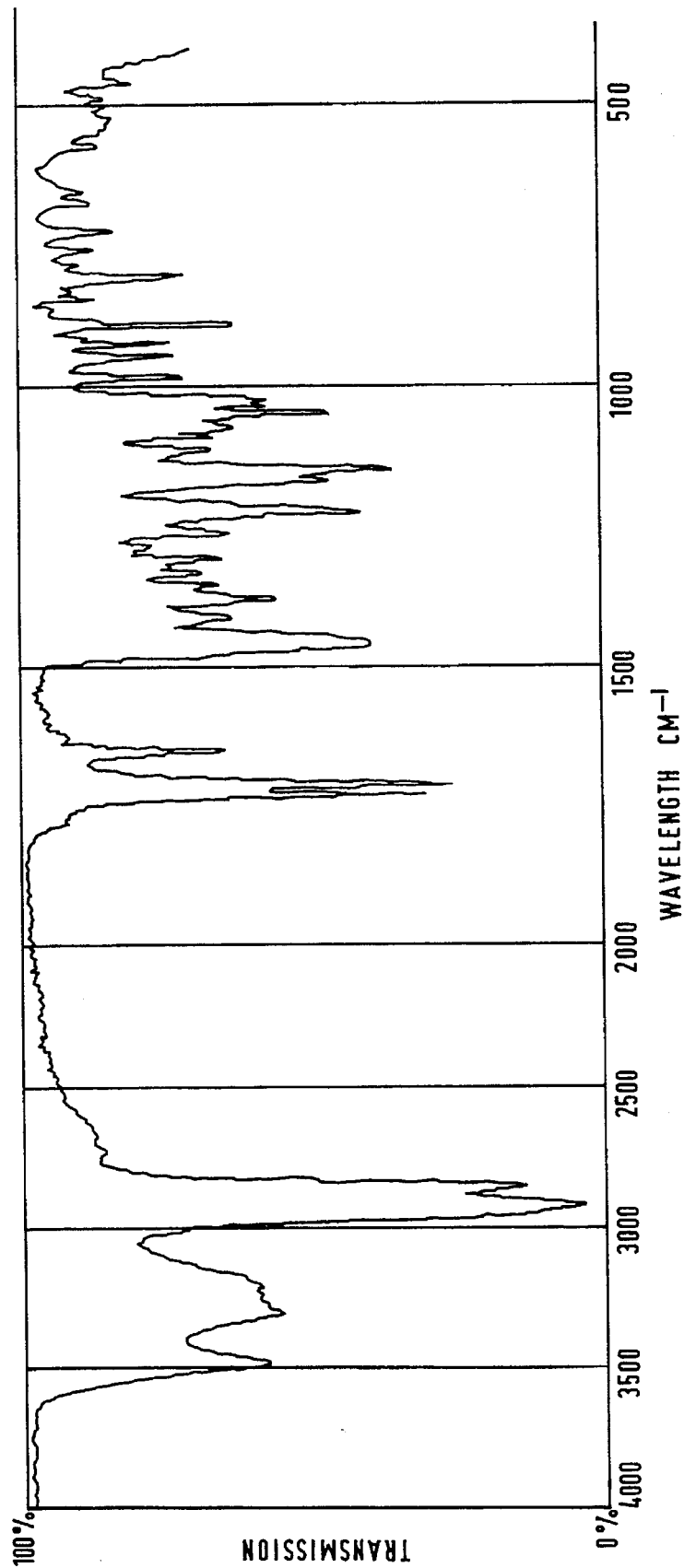

In the following description, reference is made to the accompanying drawings, in which FIG. 1 is an X-ray powder diffractogram of FORM I.
FIG. 2 is an X-ray powder diffractogram of FORM II.
FIG. 3 is an X-ray powder diffractogram of FORM III.
FIG. 4 shows the diffractogram of FORM II and III overlaid with that of FORM I.
FIG. 5 is an infrared (IR) spectrum of FORM I
FIG. 6 is an infrared (IR) spectrum of FORM II
FIG. 7 is an infrared (IR) spectrum of FORM III In one aspect the present invention provides a crystalline mupirocin polymorph (FORM II) having a melting point in the range 67°–77° C. and characterised by an X-ray powder diffractogram substantially as shown in accompanying FIG. 2.

In another aspect the present invention provides a crystalline mupirocin polymorph (FORM III) having a melting point in the range 82.5°–86° C. and characterised by an X-ray powder diffractogram substantially as shown in accompanying FIG. 3.

The melting ranges cited above were determined by DSC (Differential Scanning Colorimetry). The quoted values were obtained using a Perkin Elmer series 7 instrument operating on the power compensation principle and a Mettler instrument using the heat flux technique. The instruments gave similar results after calibration against samples from the same batches of naphthalene and of benzoic acid.

X-ray diffractograms for FORMS I, II and III are significantly different providing strong support for the existence of three discrete polymorphic forms. Accompanying FIG. 1 shows a diffractogram for FORM I, while FIG. 4 shows (over a reduced angle range) the diffractograms for FORMS II and III overlaid with that of FORM I. These diffractograms were obtained with a Philips Analytical instrument using a Cu X-ray tube operating at 40 kV and 30 mA.

A further discrimination between the polymorphs can be made by infrared spectroscopy, particularly in the case of FORMS I and III. Referring to the carbonyl stretching region at about 1725 cm$^{-1}$, in FORM I this is a single peak whereas FORM III exhibits a sharp, well-resolved doublet with peaks at 1715 and 1735 cm$^{-1}$. In addition, a broad singlet at 1175 cm$^{-1}$ in FORM I is replaced by a fairly sharp doublet at 1150 and 1170 cm$^{-1}$ in FORM III. This doublet is replaced by a singlet at 1145 cm$^{-1}$ in FORM II material. It has been found that pressure can cause transitions between the polymorphs, and therefore should be avoided during preparation of samples for testing. Accompanying FIGS. 5, 6 and 7 show IR spectra for respectively FORMS I, II AND III.

The present invention also provides processes for the preparation of the above described polymorphs.

According to the present invention crystalline mupirocin (FORM II) may be obtained by precipitating mupirocin from a solution of mupirocin in an organic solvent containing water, by the addition thereto of another organic solvent, and allowing the resultant oil to solidify.

According to the present invention crystalline mupirocin (FORM III) may be obtained by recrystallization from a solution of mupirocin in an organic solvent (or solvent mixture) while maintaining the temperature at 40° C. or above.

In the FORM II process, typical solvents are ethyl acetate or methyl iso-butyl ketone. A suitable precipitant is heptane. The procedure is normally carried out under ambient conditions. Only small amounts of water need be present, for example 1–1.5% w/v prior to addition of the precipitant. The oil is typically stirred for 8–30 hours at 15°–25° C. to achieve solidification.

In the FORM III process, a typical solvent system is a mixture of ethyl acetate or methyl iso-butyl ketone with heptane. Precipitation may be promoted by seeding with FORM I or FORM II material. The solvents need to be substantially anhydrous to avoid formation of FORM II material, and preferably before precipitation the solution is subjected to azeotropic vacuum distillation to reduce water content to less than 0.1% w/v.

The starting material for the above processes may be any other mupirocin polymorph eg FORMS I or FORM II/III as appropriate, or amorphous material.

Typically the initially precipitated crystalline slurry is stirred for prolonged periods while being maintained at 40° C. or above to achieve high yields of FORM III. The content of the slurry is assessed from time to time by removing small samples for DSC examination.

The above described procedure for producing FORM II may on occasion produce batches containing some FORM I or FORM III material.

FORM III has been found to be the most thermodynamically stable form of mupirocin known. The thermodynamically more stable polymorphic form of a compound is advantageous for maintaining crystal integrity during manufacture, storing, shipping and handling of compositions of said compound. Comparative stability data of mupirocin polymorph formulations in an ointment base is demonstrated in Example 4 below. Additionally, samples from two batches of FORM III polymorph were stored in hermetically sealed glass at 20° C. After 48 months, the mupirocin content of each sample was found by hplc assay to be 99% of the initial content. In contrast the FORM I polymorph is routinely stored at 5° C., to ensure long term stability.

Accordingly in further aspects the present invention provides a mixture of mupirocin polymorphs:

a) a mixture of FORMS I and III containing at least 5%, preferably at least 50% of FORM III;

b) a mixture of FORMS I and II containing at least 5%, preferably at least 50% of FORM II;

c) a mixture of FORMS II and III containing at least 5%, preferably at least 50% of FORM III.

For pharmaceutical purposes, each polymorph is preferably provided in a mixture which is at least 90%, preferably 95% pure, and most preferably is substantially free of other polymorphs.

The mupirocin starting material is preferably the product of aerobically culturing *Pseudomonas fluorescens* (NCIB 10586) as described in GB 1 395 907 (Beecham Group). A preferred purification procedure is described in EP 0 005 614 (Beecham Group).

This invention also provides a pharmaceutical or veterinary composition which comprises a mupirocin polymorph of FORM II or FORM III described above (hereinafter sometimes referred to simply as mupirocin for convenience) together with a pharmaceutically or veterinarily acceptable carrier or excipient.

The compositions of this invention are preferably for topical use and are accordingly formulated.

Suitable compositions include, for example, creams, lotions, ointments, dusting powders, and sprays (for example an aerosol spray emitting a powder or foam), as well as other conventional topical application formulations well known in the art.

These are described in standard text books of pharmaceutics and cosmetics, such as Harry's Cosmeticology (ed. Wilkinson & Moore, 7th edn., George Goodwin, London, 1982) and the British Pharmacopoeia.

It will be appreciated that if, in any of the formulations discussed herein, the mupirocin is presented in solution, the characteristic polymorphic form will be lost.

Preferably the mupirocin is incorporated in the composition in the form of fine particles having an average size (diameter) of less than 50 μm.

Compositions used according to the invention may contain from 0.01 to 99% mupirocin, suitably from 0.01 to 50%, preferably from 0.01 to 25% more preferably from 0.5 to 10% and especially from 1 to 3% by weight of the composition.

One suitable composition for use according to the present invention comprises mupirocin in conjunction with soft paraffin and lanolin or a derivative or synthetic equivalent thereof.

The term 'soft paraffin' as used herein includes the cream or ointment constituents white soft paraffin and yellow soft paraffin.

The term 'lanolin' as used herein includes native wool fat and purified wool fat. Derivatives of lanolin include, in particular, lanolins which have been chemically modified in order to alter their physical or chemical properties. Synthetic equivalents of lanolin include, in particular, synthetic or semisynthetic compounds and mixtures which are known and used in the pharmaceutical and cosmetic arts as alternatives to lanolin and may, for example, be referred to as 'lanolin substitutes'.

One suitable synthetic equivalent of lanolin is the material available under the Trade Mark 'Softisan' known as 'Softisan 649'. Softisan 649, available from Dynamit Nobel Aktiengesellschaft, is a glycerin ester of natural vegetable fatty acids, of isostearic acid and of adipic acid; its properties are discussed by H. Hermsdorf in Fette, Seifen, Anstrichmittel, Issue No. 84, No.3 (1982),p.p. 3–6.

Suitably such a composition comprises from 25 to 99% of the soft paraffin, preferably from 50 to 98%, more preferably from 75 to 96%. Suitably the composition comprises the lanolin or derivative or synthetic equivalent thereof in an amount of from 1 to 25%, preferably from 1 to 15%, more preferably from 3 to 7%. In addition, such a composition may contain liquid paraffin in an amount of from 0 to 20%.

The term 'liquid paraffin' as used herein includes any form of liquid paraffin suitable for pharmaceutical or veterinary topical use.

One particularly suitable such composition for use according to the present invention comprises from 1 to 3% of mupirocin, from 65 to 96% (preferably from 75 to 96%) of white soft paraffin, from 0 to 15% of liquid paraffin, and from 3 to 7% of lanolin or a derivative or synthetic equivalent thereof. Such a composition may suitably be presented as an ointment for application to the skin.

A second particularly suitable composition for use according to the present invention comprises from 1 to 3% of mupirocin, from 25 to 60% of liquid paraffin, from 20 to 50% of water, from 3 to 30% (preferably from 10 to 30%) of emulsifier, and, optionally, one or more conventional auxiliaries, such as a preservative. Such a composition may suitably be presented as a cream or lotion for application to the skin.

Suitable emulsifiers for use in such a composition include, for example, stearyl alcohol, cetyl alcohol, polyoxyethylene ethers having surfactant properties such as for example, polyethylene glycol (1000) monocetyl ether (ie cetomacrogol 1000), polyethoxylated sorbitol monoesters, such as for example polysorbate 60 and polysorbate 80 and other surfactants conventionally used as emulsifiers in pharmaceutical preparations, especially in creams.

Suitable preservatives for use in such a composition include, for example, phenoxyethanol, and other preservatives conventionally used in pharmaceutical preparations, especially in creams.

The composition used according to the present invention may comprise additional therapeutic agents such as antimicrobial, antibiotic, antibacterial, antifungal, antiviral, and antiinflammatory agents, for example from 1 to 3% of chlortetracycline, idoxuridine, phenazone, hydrocortisone or polymyxin, provided that such additional components are compatible with the mupirocin and the other components. Mupirocin shows a tendency to undergo rearrangement reactions in the presence of acids and accordingly acidic agents are unlikely to be compatible with mupirocin.

The compositions may also comprise appropriate conventional additives, for example preservatives, emulsifiers, solvents to assist drug penetration, and emollients.

For topical application to the ear, the mupirocin may be made up into a suspension in a suitable liquid carrier, such as water, glycerol, diluted ethanol, propylene glycol, polyethylene glycol or fixed oils.

For topical application to the eye, the mupirocin is formulated as a suspension in a suitable, sterile aqueous or non-aqueous vehicle. The mupirocin may also be applied to the skin by aerosol.

The dosage employed for compositions administered topically will, of course, depend on the size of the area being treated. For the ears and eyes each dose will typically be in the range from 10 to 100 mg of mupirocin.

The compositions used according to the invention may be produced by conventional pharmaceutical or veterinary techniques. Thus, for example, ointments and creams may conveniently be prepared by mixing together at an elevated temperature, preferably 60°–70° C., the components constituting the vehicle. The mixture may then be cooled to room temperature, and, after addition of any further ingredients, stirred to ensure adequate dispersion. The mupirocin may be added during the hot preparation of the base, or may be added together with the additional ingredients after cooling of the base.

A suitable sterilisation procedure may be included in the above procedure if necessary. Alternatively raw materials may be obtained in sterile condition and the formulation may be produced aseptically.

If necessary the composition may be milled at any suitable stage of the process using conditions that do not effect a polymorphic transition.

Crystalline polymorphs of the present invention are of use in therapy. Accordingly, in a further aspect, the present invention provides crystalline mupirocin in any one of the polymorphic Forms II or III hereinbefore described, for use in therapy. The present invention also provides a method of treatment of humans or animals which method comprises administering to a human or animal in need thereof an effective non-toxic amount of crystalline mupirocin polymorph of Form II or Form III as hereinbefore described.

The compositions comprising mupirocin used according to the invention are active against those organisms responsible for the majority of skin infections, for instance *Staphylococcus aureus,* including methicillin-resistant strains, other Staphylococci, and Streptococci. They are also active against Gram-negative organisms such as *Escherichia coli* and *Haemophilus influenzae.* Compositions according to the invention may be usefully used to treat bacterial skin infections such as impetigo, folliculitis and furunculosis.

The compositions herein before described and comprising mupirocin in an amount that corresponds to at least the saturation solubility of mupirocin in the carrier at ambient temperature are also antifungally active, in particular against filamentous fungi. They are useful in combating fungal infections in animals, including humans. They may, for example, be used in treating topical fungal infections in man caused by, among other organisms, species of Trichophyton, Trichosporon, Hendersonula, Microsporum, Epidermophyton, and Pityrosporum. They may also be used in the treatment of a variety of other fungal infections caused by, for example Aspergillus, Coccidioides, Paracoccidioides, Histoplasma and Blastomyces species.

Corresponding compositions and their anti-fungal use for the FORM I polymorph are described in EP 0 251 434 (Beecham Group).

In such compositions, mupirocin is present in a composition in an amount of at least 100% by weight, advantageously 101% by weight, preferably at least 110% by weight, and more especially at least 150% by weight, of its saturation solubility in the carrier at ambient temperature.

The present invention also provides a method for improving the weight gain and feed utilisation efficiency of livestock, which method comprises administering to livestock a growth promoting, non-toxic amount of crystalline mupirocin as polymorph form II or III described above. Reference is directed to GB 2 097 670 (Beecham Group) which discloses the use of mupirocin and its salts and esters as a growth promoter for livestock, for appropriate procedures.

The mupirocin polymorphs may be administered to any livestock for example pigs, poultry and ruminants such as cattle and sheep. It is particularly suitable for improving the weight gain and feed utilisation efficiency of pigs.

The mupirocin polymorphs may be administered orally, preferably in the feedstuff or drinking water provided for the livestock. Conveniently it is administered in the feedstuff at from 2 to 300 ppm suitably less than 100 ppm, for example from 10 to 40 ppm.

For administration in feedstuff the crystalline mupirocin polymorph is conveniently formulated as a premix in association with a suitable carrier.

Accordingly in a further aspect, the present invention provides a veterinarily acceptable premix formulation comprising mupirocin as polymorph FORMS II or III described above in association with a veterinarily acceptable carrier.

Suitable carriers are inert conventional agents such as powdered starch. Other conventional premix carriers may also be employed.

No toxicological effects are indicated when the polymorphs of this invention are administered in dosage angles as described above.

The following Examples illustrate the invention.

EXAMPLE 1

Preparation of Mupirocin FORM II 50 g of mupirocin (FORM I) was slurried in 500 ml methylisobutyl ketone (MIBK) and heated to 32° C. to dissolve. The solution was allowed to cool to 24° C. over ca 1 hour. 5 ml distilled water was added followed by 500 ml n-heptane over ca 2 hours. The material began to oil out to form a thin gummy oil. On stirring overnight at 25° C. the material had changed to a filterable solid. The product was filtered, washed with 1:1MIBK/heptane and dried in a vacuum oven overnight at 40° C. Yield =45.0 g

EXAMPLE 2

Preparation of Mupirocin FORM III 50 g of mupirocin (FORM I) was slurried in 500 ml ethyl acetate and 400 ml n-heptane. The slurry was heated to 54° C. to dissolve, allowed to cool slowly over ca 1 hour to 40° C. and seeded with the starting material. The slurry was held at 40° C. for the rest of the procedure. After the product had precipitated, small samples were taken, filtered and dried, then examined by DSC. Although at first the precipitate was entirely Form I, it was slowly converted to Form III.

The product was filtered, washed with 1:1 ethyl acetate/ heptane and dried in a vacuum oven overnight at 40° C. Yield =38.6 g

EXAMPLE 3

Preparation of Mupirocin FORM III 50 g of mupirocin (FORM I) was slurried in 500 ml ethyl acetate and 400 ml n-heptane. The slurry was heated to 52° C. to dissolve, allowed to cool slowly over ca 1 hour to 40°

C. and seeded with product material from Example 2. The slurry was held at 40° C. for the rest of the experiment. After the product had precipitated, small samples were taken, filtered and dried, then examined by DSC. At first the precipitate was mainly Form I with approximately 20% Form III, but was slowly converted to Form III. A stir time of 3 days was required until the material was 100% Form III.

The product was filtered, washed with 1:1 ethyl acetate/heptane and dried in vacuum oven overnight.
Yield =39.0 g

EXAMPLE 4

Comparative Stability Data

Formulations containing either FORM I or FORM III (two batches) of mupirocin (2.2%) in a common base (OB2) containing white soft paraffin (92.96%) and Softisan 649 (4.89%) (to imitate an appropriate pharmaceutical formulation of mupirocin) were tested for storage stability over 45 months, at 20°, 25° and 30° C. The resultant data is shown in TABLE I below:

TABLE I

|  | Mupirocin content - % initial 45 months, 20° C. | Mupirocin content - % initial 45 months, 250° C. | Mupirocin content - % initial 45 months, 30° C. |
| --- | --- | --- | --- |
| Form III | 99 | 97 | 97 |
| Form III | 102 | 99 | 101 |
| Form I | 100 | 93 | 66 |

As indicated above, FORM III has been characterized by over three years crystalline stability testing.

What is claimed is:

1. A crystalline mupirocin polymorph (FORM III) having a melting point in the range 82.5°–86° C. and characterised by an X-ray powder diffractogram substantially as shown in accompanying FIG. 3 and IR spectrum substantially as shown in accompanying FIG. 6.

2. A mixture of mupirocin polymorphs that contains at least 90% by weight of the polymorph of claim 1.

3. A pharmaceutical or veterinary composition comprising an anti-infective amount of a mupirocin polymorph of claim 1 together with a pharmaceutically or veterinarially acceptable carrier.

4. A composition according to claim 3 comprising from 1 to 3% of mupirocin polymorph, from 65 to 96% of white soft paraffin, from 0 to 15% of liquid paraffin and from 3 to 7% of lanolin or a derivative or synthetic equivalent thereof.

5. A composition according to claim 3 comprising from 1 to 3% of mupirocin polymorph, from 25 to 60% of liquid paraffin, from 20 to 50% of water and from 3 to 30% of emulsifier.

6. A method of combatting bacterial or fungal infections in humans or animals which comprises administering an effective amount of a mupirocin polymorph as defined in claim 1 to an infected human or animal.

7. A process for preparing a crystalline mupirocin polymorph (FORM III) as defined in claim 1 which comprises recrystallizing mupirocin from a solution of mupirocin in an organic solvent (or solvent mixture) while maintaining the temperature at 40° C. or above.

8. A process according to claim 7 in which the organic solvent has a water content of less than 0.1% w/v.

9. A process according to claim 7 in which the initially formed crystalline precipitate is stirred while maintaining the temperature at 40° C. or above until the crystalline precepitate is substantially all FORM III.

* * * * *